United States Patent [19]

Apple

[11] 4,015,479
[45] Apr. 5, 1977

[54] SAMPLING PROBE AND METHOD

[75] Inventor: Glenn Dwight Apple, Newark, Del.

[73] Assignee: E. I. Du Pont de Nemours and Company, Wilmington, Del.

[22] Filed: May 13, 1976

[21] Appl. No.: 686,645

[52] U.S. Cl. .......................... 73/422 R; 23/232 R; 73/421.5 A
[51] Int. Cl.[2] ........................................ G01N 1/22
[58] Field of Search ... 73/422 R, 421.5 A, 421.5 R; 23/232 R, 254 R

[56] References Cited

UNITED STATES PATENTS

| | | | |
|---|---|---|---|
| 3,559,491 | 2/1971 | Thoen | 73/421.5 R |
| 3,718,429 | 2/1973 | Williamson, Jr. | 23/232 R |
| 3,807,233 | 4/1974 | Crawford | 73/421.5 R |
| 3,819,330 | 6/1974 | Creighton | 23/254 R X |
| 3,959,341 | 5/1976 | Dunn | 23/254 R X |

FOREIGN PATENTS OR APPLICATIONS 1,206,178   7/1960   Germany .................... 73/422 R Primary Examiner—Richard C. Queisser
Assistant Examiner—Joseph W. Roskos

[57] ABSTRACT

A remote sampling probe, for withdrawing fluid from a pipe through a filter capped sample tube extending into the pipe, is provided with a housing extending into the pipe and surrounding the outer portions of the sample tube, a source of relatively high pressure, controlled temperature secondary fluid, and a means for alternately introducing the secondary fluid into the housing to control the temperature of the sample withdrawn from the pipe and into the sample tube to backflush the filter.

9 Claims, 5 Drawing Figures

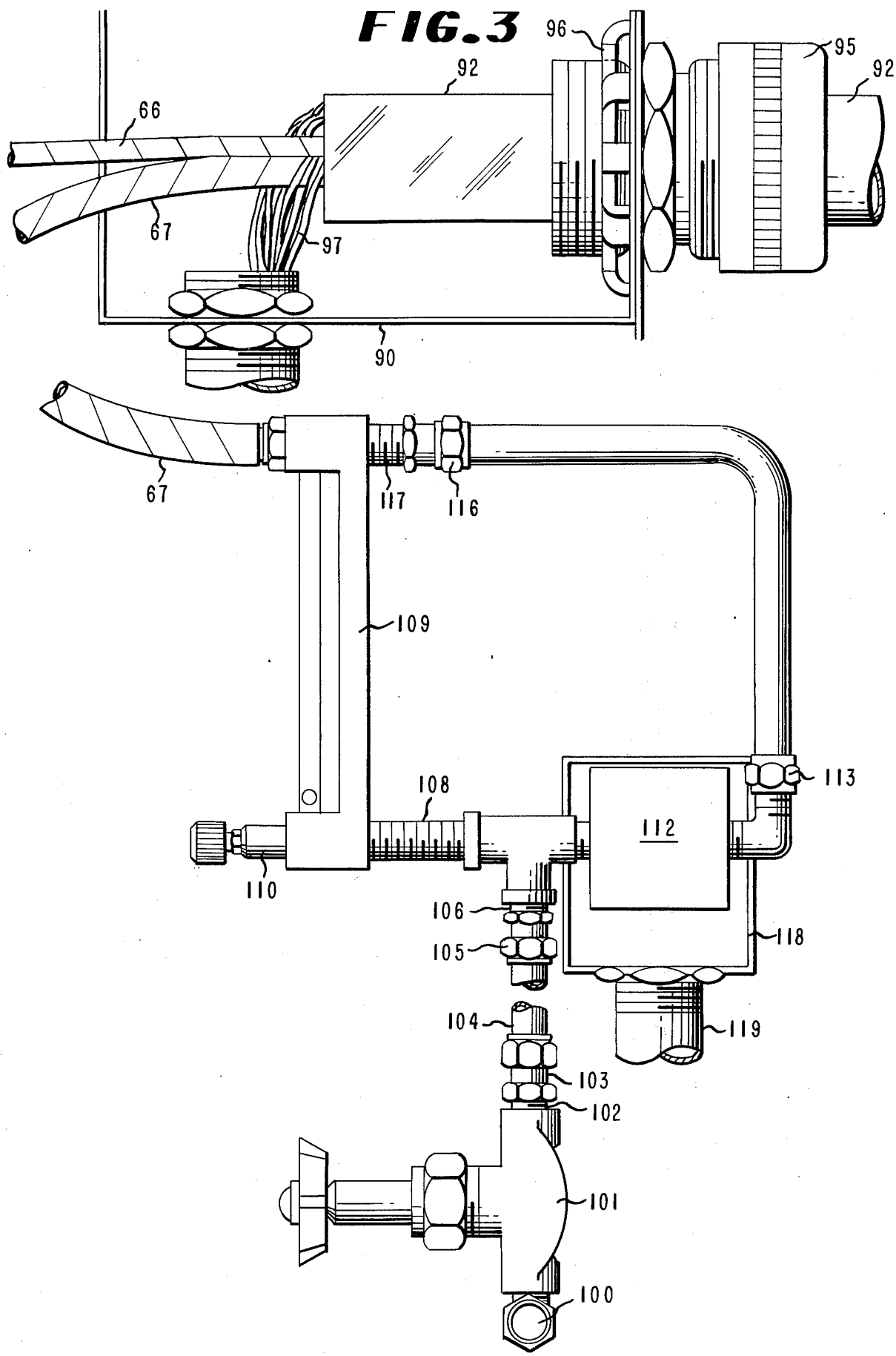

SAMPLING PROBE AND METHOD

BACKGROUND OF THE INVENTION

1. Field of the Invention:

The present invention relates to probes for sampling fluids located in a wall confined region, such as a pipe. More particularly, it relates to remote sampling probes for sampling stack emission gases.

2. Discussion of the Prior Art:

Sampling probes generally comprise a sample tube extending into a wall confined region where the fluid of interest (hereinafter referred to as the primary fluid) is located, usually as a flowing stream of gas. If the pressure in the confined region is high enough, the primary fluid will flow through the sample tube to a detecting station. If the pressure in the confined region is insufficient, a vacuum is applied to the sample tube to withdraw a portion of the primary fluid from the confined region and to conduct it to a detecting station containing a measuring device, such as a process stream photometer, designed to measure the concentration of a constituent or constituents of the primary fluid.

Often the point at which the sampling takes place is remote from the measuring device. Such is the case when measuring stack emission gases using ground based equipment. Since the measured concentration of the various constituents of the primary fluid is dependent on the temperature of the fluid, the temperature of the fluid reaching the measuring device should be equal, or at least proportional, to that of the fluid in the confined region. Hence, when the measuring device is remotely located from the sample point, the conduit connecting the sample probe to the measuring device is maintained at a controlled temperature, commonly by an electrically heated conduit. However, it is difficult to electrically control the temperature of the entire sample probe, particularly when that probe contains a calibration fluid inlet.

Furthermore, since emisson gases and other primary fluids often contain particulate material which would either clog the sample conduit or interfere with the measurement, the end of the sample probe which extends into the confined region is usually capped with a filter. These filters have a tendency to become clogged with the particulate matter in the primary fluid, and this effects the precision of the measurement.

SUMMARY OF THE INVENTION

The present invention relates to a sampling probe and method in which probe temperature control and filter maintenance are accomplished, simply and effectively, by providing a probe for sampling a primary fluid (either gas or liquid) located in a confined region defined by at least one wall (e.g., a pipe), comprising a sample tube having a first end extending through the wall into the confined region and a second end located outside the confined region and a filter attached to the first end of the sample tube, the improvement wherein the probe further comprises:

a. a housing extending through the wall into the confined region and surrounding that portion of the sample tube located outside of the confined region, the housing being in substantially fluid-tight association with the wall and having at least one orifice connecting the interior of the housing to the confined region at a position remote from the filter;

b. a source of relatively high pressure, temperature controlled secondary fluid; and c. a valving means alternately connecting the source of secondary fluid to the interior of the housing or to the second end of the sample tube.

In the preferred embodiment, the probe also comprises a source of vacuum for withdrawing a portion of the primary fluid in the confined region through the filter and sample tube, and the valving means alternately connects the source of vacuum to the second end of the sample tube and the source of secondary fluid to the interior of the housing or venting the source of vacuum and connecting the source of secondary fluid to the second end of the sample tube.

In a still more preferred embodiment, the valving means is a four-port, plug valve with bleed grooves formed therein separating the vacuum and high pressure fluid ports, and preventing cross-port leakage or contamination of the primary fluid.

The invention also provides an improved method of sampling a primary fluid located in a confined region defined by at least one wall by the steps of providing a sample tube with a first end having a filter attached thereto extending through the wall into the confined region and a second end located outside the confined region, and withdrawing a portion of the primary fluid from the confined region through the filter and the sample tube, the improvement comprising the steps of:

a. providing a housing extending through the wall into the confined region and surrounding that portion of the sample tube located outside of the confined region, the housing being in substantially fluid-tight association with the wall and having at least one orifice connecting the interior of the housing with the confined region at a position remote from the filter;

b. introducing a relatively high pressure, controlled temperature secondary fluid into the housing to control the temperature of the sample tube and the fluid being withdrawn through it; and c. alternately introducing the secondary fluid into the second end of the sample tube to backflush the filter.

BRIEF DESCRIPTION OF THE DRAWINGS

The present invention will be described by reference to the following figures in which:

FIG. 3 is a detailed view of one embodiment of a secondary fluid supply mechanism which can be used with the apparatus shown in FIGS. 1 and 2;

DESCRIPTION OF THE PREFERRED EMBODIMENT

Although the present invention is useful whenever a fluid (e.g., either a gas or a liquid) in a confined region is to be sampled, for convenience, the following discussion will be limited to a probe for sampling gases, such as emission gases, flowing through a pipe, such as a stack.

Figure 1:
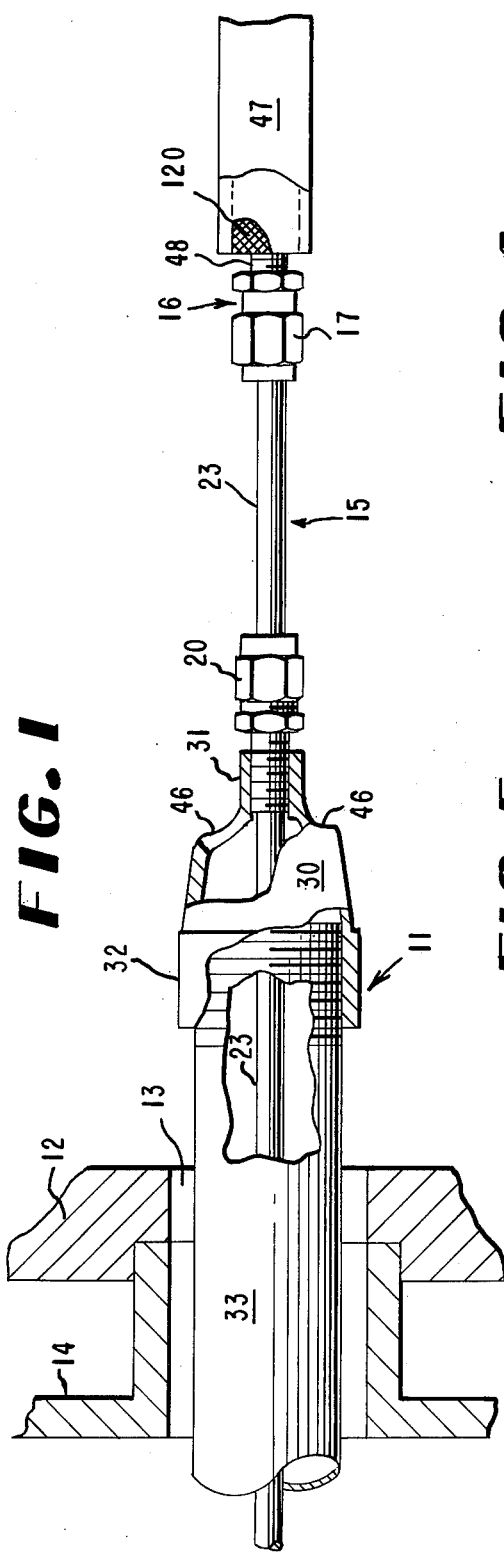
FIG. 1 is a partially exposed side view of one embodiment of the apparatus of the present invention showing that portion of the sample probe disposed within the confined region.
Figure 2:
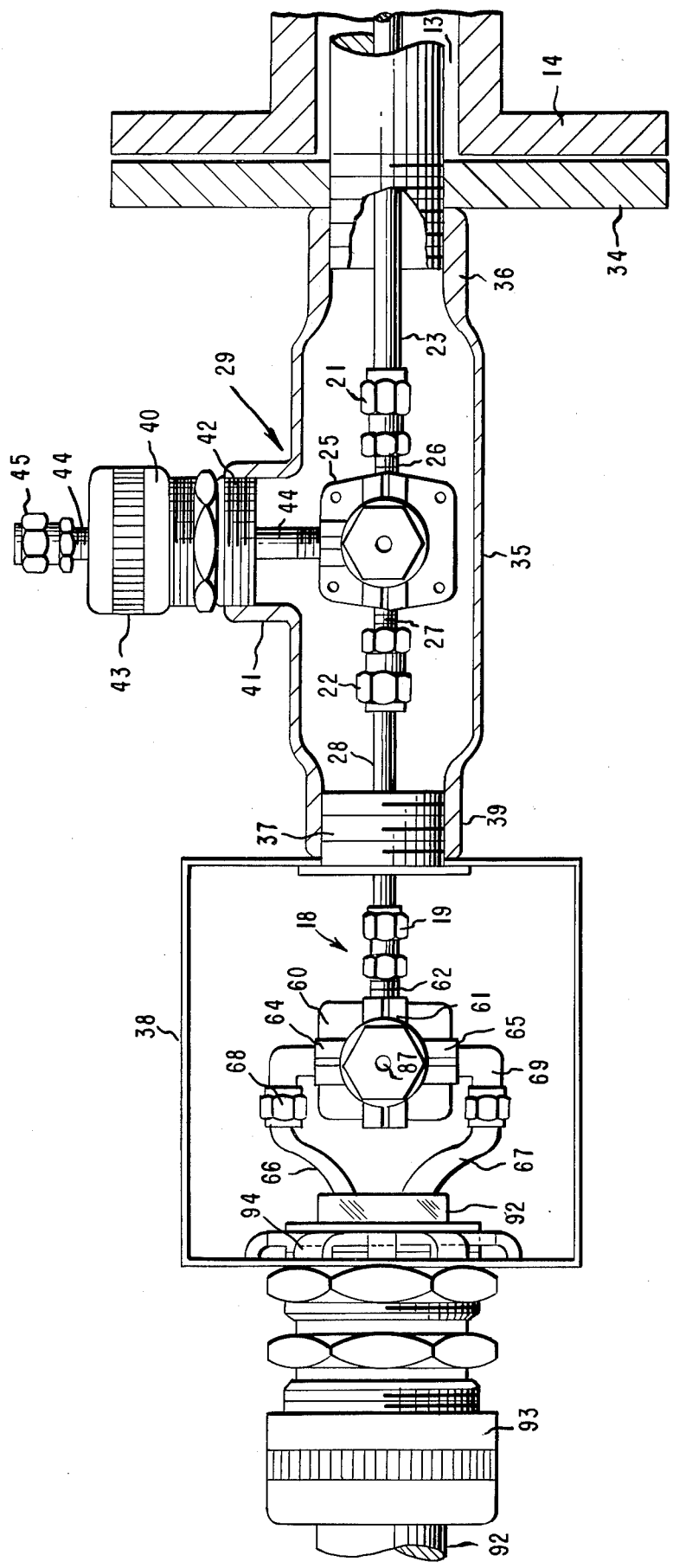
FIG. 2 is a partially exposed side view of the embodiment of the apparatus of the present invention, showing that portion of the sample probe disposed outside of the confined region.

In FIGS. 1, a sample probe, indicated generally by 11, has been inserted into a confined region defined by pipe wall 12, through an orifice 13 provided for that purpose. A flange 14 on pipe wall 12 is provided to support the sample probe. The term sample probe shall be used, hereinafter, to indicate the structure shown in FIGS. 1 and 2 extending from connector 93 to filter 47.

In the embodiment shown, sample probe 11 comprises a segmented sample tube, indicated generally by 15, and extending from a first end 16 defined by connector 17 to a second end 18 defined by connector 19. A filter 47 is connected to the first end 16 of sample tube 15 by a threaded nipple 48 which engages connector 17. Connectors 17, 19, 20, 21 and 22 are commercially available, composite connectors with external threads on one end and Swagelock compression fittings on the other end. Between connectors 17 and 20 is an extension tube 23 which is held by the compression fitting portions of connectors 17 and 20. Extension tube 23 passes through compression fitting 20, extending to connector 21 where it is grasped by the compression fitting portions of connector 21. Between connectors 21 and 22 is a three-way valve 25, the function of which will be described later. Internally threaded openings 26 and 27 connects two ports of valve 25 to the external threaded ends of connectors 21 and 22. Finally, a third extension tube 28 connects the compression fitting portions of connectors 19 and 22.

The construction of these parts, and all of the parts described hereafter, are well known to those skilled in the art. The valves and connectors are commercially available. If the gases to which they are subjected are hot, they can be made of stainless steel, or any other suitable material.

Surrounding the external portions of sample tube 15 and extending into the interior of the pipe through orifice 13, is a housing indicated generally by 29. This housing can be a single housing, but in the embodiment illustrated, it comprises a number of separate parts. As illustrated, the housing comprises a cap 30 and an extension tube 33 both of which are threaded at both ends. An internally threaded protrusion 31, one one end of cap 30 engages the threaded end of connector 20. The other internally threaded protrusion 32 on cap 30 engages one of the externally threaded ends of extension tube 33. The other externally threaded end of extension tube 33 is connected to a flange 34 which is used to connect sample probe 11 to pipe 12 in conjunction with flange 14 by bolts, not shown.

Housing 29 also comprises a primary casing 35 and a secondary casing 38. Primary casing 35 has three internally threaded protrusions. Protrusion 36 is held in contact with flange 34 by the threads of extension tube 33. A flanged nut 37 is used to connect secondary casing 38 to primary casing 35, in gas-tight association, by threaded engagement with protrusion 39. Finally, connector 40, which has an externally threaded end 42 and a compression fitting end 43, is provided. The externally threaded end 42 of connector 40 engages protrusion 41 of primary casing 35. An elongated nipple 44 which is threaded at both ends connects the third port of valve 25 to a composite connector 45 which has an internally threaded end and a compression fitting end. Nipple 44 is held in gas-tight association with connector 40 by compression fitting 43.

Housing 29 completely surrounds that portion of sample tube 15 which is disposed outside of pipe 12. The housing is held in substantially leak-tight association with the walls of pipe 12 by flange 34, and extends into the interior of pipe 12 through orifice 13. Inside of the pipe, the housing terminates in cap 30 which has a plurality of orifices 46 connecting the interior of the housing to the interior of the pipe. These orifices are located at a position remote from filter 47. Since secondary gas will be introduced into pipe 12 through orifices 46 which primary gas is being withdrawn from pipe 12 through filter 47, the orifices 46 should be located far enough from filter 47 so that the introduction of secondary gas at this point will have little or no effect on the composition of the primary gas sampled by the filter. This is what is meant by the term remote. The distance will vary depending on the circumstances.

Filter 47 is of a type well known to those skilled in the art. Its filtering capacity is illustrated generally by a screen 120 located in the filter.

The second end 18 of sample tube 15 is connected to a valving means 60, which in the embodiment illustrated, is a variable setting, four-port, plug valve disposed within secondary casing 38 of housing 29. One port 61 of this four-port valve 60 is connected to connector 19 by a threaded extension 62 on that fitting. A second port 63 of the four-port valve connects to the interior of housing 29. The third and fourth ports, 64 and 65, respectively, are connected to tubes 66 and 67, respectively, through connectors 68 and 69, respectively.

Figure 4:
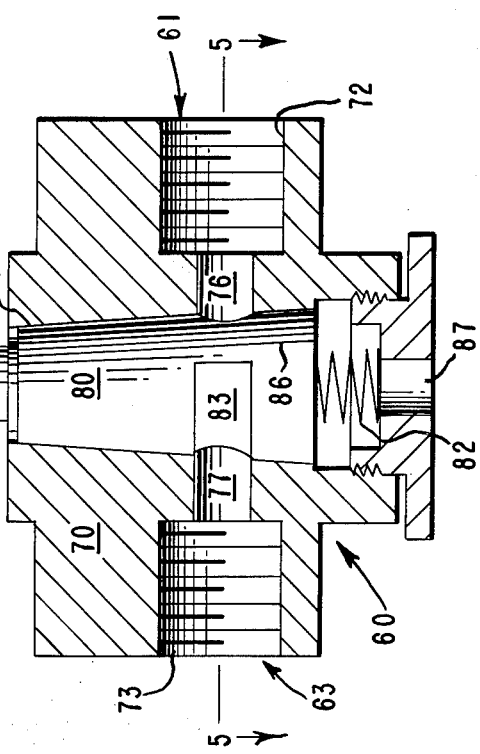
FIG. 4 is a side view, shown in partial cross section, of one embodiment of a valving means which can be used with the apparatus shown in FIGS. 1 and 2.
Figure 5:
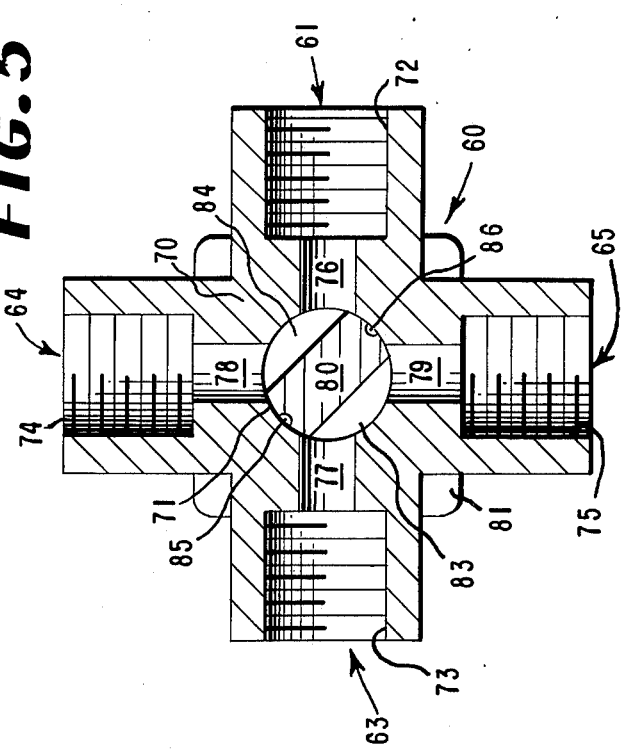
FIG. 5 is a section view of the valving means of FIG. 4 taken along the lines 5—5.

The construction of valve 60 can best be visualized by reference to FIGS. 4 and 5. Valving means 60 comprises a housing 70 with a tapered channel 71 passing through it. The four ports 61, 63, 64, and 65 of the valve are connected to this central channel 71 by four internally threaded recesses 72, 73, 74, and 75, respectively, and four connecting channels 76, 77, 78, and 79, respectively. Located in central channel 71 is a tapered cylindrical plug 80 which fits in close, leak-tight, association with the walls of channel 71. The plug is held in such association by a spring 82 and a cap 81 which threadedly engages housing 70 and holds spring 82 against plug 80. Plug 80 is provided with two slots, 83 and 84, which are located proximate to connecting channels 76, 77, 78, and 79. In the setting shown in FIGS. 4 and 5, these two slots, 83 and 84, connect channels 77 and 79 and channels 76 and 78, respectively. When plug 80 is rotated by 90°, slots 83 and 84 alternately connect channels 77 and 78 and channels 76 and 79, respectively. Plug 80 also contains two bleed grooves 85 and 86 which extend longitudinally along the plug to provide a path for any gas trapped in that groove to the interior of the housing through a hole 87 formed in cap 81. These bleed grooves effectively insulate the vacuum ports of valve 60 from the high pressure ports of valve 60 and prevent cross-port leakage. Finally, the valve contains a protrusion 88 which can be used to rotate plug 80. Protrusion 88 may be a handle, but in the embodiment illustrated, valve 60 is a remotely operated valve, and hence protrusion 88 indicates generally the electromechanical structures needed to operate the valve.

Tube 66 is a flexible tube, one end of which is connected to port 64 of valve 60 and the other end of which is connected to the detecting station. If the pressure of the primary gas in the pipe is high enough, the gas will flow through tube 66 to the detecting station.

Usually, however, a source of vacuum must be provided to draw the primary gas from the pipe to the detector. In this case, the other end of tube 66 is connected to a source of vacuum. The discussion which follows will, for convenience, be limited to this latter situation. When valve 60 is in the setting shown in FIG. 5, tube 66 is connected through ports 61 and 64 of valve 60 directly to the second end of the sample tube, and through that tube and filter 47 to the interior of the pipe. Under the action of the vacuum, a portion of the primary fluid flowing in the pipe will be drawn from the interior of the pipe through filter 47 and sampling tube 15 into tube 66. Tube 67 is also a flexible tube. One end of this tube is connected to a source of relatively high pressure, controlled temperature secondary gas, and the other end of tube 67 is connected to port 65 of valve 60. When valve 60 is in the setting shown in FIG. 5, tube 67 is connected through ports 63 and 65 of valve 60 to the interior of housing 29. It is vented from the housing through orifices 46 in cap 30 to the interior of the pipe. When plug 80 of valve 60 is turned by 90°, tube 66 will be connected through the valve to the interior of the housing through port 63. The vacuum provided by tube 66 will then draw primary fluid from the interior of the pipe through orifice 46 into the housing. More importantly, however, tube 67, which is connected to the source of secondary gas, will be connected to the second end of sample tube 15 through valve 60. Secondary gas will then flow through sample tube 15 and filter 47 into the interior of the pipe.

Conduits 66 and 67 are fed from secondary casing 38 to an electrical housing 90 through a connecting cable 92. Cable 92 is connected to secondary casing 38 by a compression fitting 93 which is attached to casing 38 by nut 94. In the same manner, conductor 92 is attached to electrical housing 90 by a compression fitting 95 with a threaded end connected to housing 90 by a nut 96. Cable 92 serves primarily as a conduit for tubes 66, 67. However, since valves 25 and 60 are remotely operated valves, cable 92 also serves as a conduit for the electrical wires 97 used to operate the valves. The actual electrical connection to the valve are not shown since electrically controlled valves suitable for use as valves 25 and 60 are well known to those skilled in the art. Cable 92 is electrically heated so that conduits 66 and 67 will be maintained at a controlled temperature. Cables such as cable 92, with the enclosed electrical connections and temperature controlled conduits 66 and 67, are commercially available from Technical Heaters, Inc.

Conduit 66 is normally a vacuum line. It is used to draw a portion of the primary fluid flowing through pipe 12 into the detecting station. Detecting stations with an aspirating vacuum attachment to draw the sample from a remote location into the detecting station are well known to those skilled in the art and will not be described further here except to say that the systems described in U.S. Pat. No. 3,718,429 which issued on Feb. 27, 1973 to J. A. Williamson, Jr., can be used as the vacuum source and detecting station. Such systems, sold as the 400 Photometric Series, are available commercially from E. I. du Pont de Nemours and Company.

Conduit 67 is the high pressure secondary gas conduit. A secondary gas is supplied to an input 100. Any suitable, noncontaminating secondary gas, such as air, can be used. Its pressure is regulated by a valve 101, and it is passed through a conduit 104 to a tee 107. Valve 101, conduit 104, and tee 107 are held together by threaded nipples 102 and 106 and by compression fittings 103 and 105. From tee 107, the high pressure gas is normally fed through a flowmeter 109 directly to conduit 67. Valve 110 on flowmeter 109 controls the flow of secondary gas through conduit 67 and hence into housing 29. Flowmeter 109 is connected to tee 107 by threaded fitting 108.

A secondary path is also provided for the secondary gas from tee 107 to conduit 67. Tee 107 is connected by threaded fitting 111 to a valve, indicated generally by 112, and from that valve through a conduit 115 to the upstream side of flowmeter 109. Various compression fittings 113 and 116 and a threaded nipple 117 are provided for this purpose. Valve 112 is an electrically controlled valve contained in an electrical housing 118. Electrical wires, not shown, are introduced into this housing through conduit 119. Valve 112 is ganged with valve 60 so that when valve 60 changes from the position shown in FIG. 5 to its alternate position, valve 112 opens.

The embodiment of the present invention illustrated in the figures operates as follows. A vacuum is constantly applied to conduit 66 as described in U.S. Pat. No. 3,718,429 (supra). Valve 60 is in the position shown in FIG. 5, and valve 25 is set so that conduits 23 and 28 are connected together and conduit 44 is shut off. In this configuration, primary fluid is withdrawn from pipe 12 under the action of the vacuum applied to conduit 66. It is drawn through filter 47, sample tube 15, ports 61 and 64 of valve 60, and finally through the remainder of conduit 66 to the detecting station where the measurements are made. At the same time, a relatively high pressure secondary gas is supplied from conduit 67 to housing 29. The secondary gas is heated by passing through heated conduit 92. The secondary gas bathes the interior of housing 29 and hence the components contained in housing 29 with gas at a temperature above the condensation point and near to the temperature of the gas in the pipe. A temperature of between about 150° C. and about 200° C. is normally used. Normally, valve 112 is closed and valve 110 is adjusted so that the pressure of the secondary gas entering conduit 67 is sufficient to force the secondary gas through the connecting lines and the housing and into the pipe through orifices 46. A pressure between about 60 and about 150 psig is normally used at inlet 100.

After a certain time, depending upon the particular nature of the contaminants in pipe 12, filter 47 will become clogged. At this point, or at periodic intervals, as desired, both valves 112 and valve 60 are activated. Valve 60 is changed to its alternate setting and valve 112 opens. In this configuration, vacuum applied through conduit 66 is vented to the interior of casing 38 through ports 63 and 64 of valve 60. It could, of course, be vented instead to the atmsophere. At the same time, relatively high pressure secondary gas is introduced into pipe 12 through conduit 67, ports 65 and 61 of valve 60, sample tube 15, and filter 47. As it passes through the filter, it acts to backflush the filter and remove the particulate material clogging the screen 120. Valve 101 is adjusted to provide the flow and pressure needed to accomplish this. A pressure of between about 60 and about 150 psig is normally used.

Valve 112 is provided because, under normal circumstances, the pressure of the secondary gas flowing through housing 29 and into pipe 12 need not be very high. However, when used to backflush filter 47, the pressure of the secondary gas must be increased. Therefore, relatively high pressure gas is introduced into inlet 100, and valve 110 is used to throttle its flow as it is introduced into housing 29. When valve 112 is opened, however, the throttling effect of valve 110 is overcome and full pressure of the gas entering inlet 100 is applied to conduit 67.

Some means to calibrate most detecting systems must be provided. This is usually done by introducing a calibration gas into the detector in place of the sample gas. This is most easily done at the detecting station, but State and Federal Regulations provide that when calibrating remote sample probe systems, the calibration gas must be introduced into the system at a point as close as possible to the pipe. It must be introduced into a port, such as that provided by connector 45 in FIG. 2, which is located proximately to the entrance to the pipe. The calibration gas introduced into port 45 normally does not enter sample tube 15 because valve 25 is set so that conduit 44 is not connected to the sample tube indicated by conduits 23 and 28. Valve 25, which is a remote control valve, can, however, be activated to connect conduit 44 to conduit 28 and to shut off conduit 23, in which case the calibration gas, not the primary gas, is drawn by the vacuum through conduit 66 into the detecting station.

The above description is intended to teach those skilled in the art how to build and operate the sample probe of the present invention. It is not intended to limit the scope of the invention as set forth in the appended claims.

What is claimed is:

1. In a probe for sampling a primary fluid located in a confined region defined by at least one wall, said probe comprising: a sample tube having a first end extending through the wall into the confined region and a second end located outside the confined region and a filter attached to the first end of said sample tube, the improvement wherein said probe further comprises:
   a. a housing extending through the wall into the confined region and surrounding that portion of said sample tube located outside of the confined region, said housing being in substantially fluid-tight association with the wall and having at least one orifice connecting the interior of said housing to the confined region at a position remote from said filter;
   b. a source of relatively high pressure, temperature controlled secondary fluid; and
   c. valving means alternately connecting said source of secondary fluid to the interior of said housing, or to the second end of said sample tube.

2. In a probe for sampling a primary fluid located in a confined region defined by at least one wall, said probe comprising: a sample tube having a first end extending through the wall into the confined region and a second end located outside the confined region, a filter attached to the first end of said sample tube, and a source of vacuum for withdrawing a portion of the primary fluid in the confined region through said filter and said sample tube, the improvement wherein said probe further comprises:
   a. a housing extending through the wall into the confined region and surrounding that portion of said sample tube located outside of the confined region, said housing being in substantially fluid-tight association with the wall and having at least one orifice connecting the interior of said housing to the confined region at a position remote from said filter;
   b. a source of relatively high pressure, temperature controlled secondary fluid; and
   c. valving means alternately connecting said source of vacuum to the second end of said sample tube and said source of secondary fluid to the interior of said housing, or venting said source of vacuum and connecting said source of secondary fluid to the second end of said sample tube.

3. The probe of claim 2 wherein said valving means is a four-port, plug valve having bleed grooves formed therein, separating the vacuum and high pressure fluid ports.

4. The probe of claim 2 wherein said source of secondary fluid comprises means to vary the pressure of the secondary fluid whereby the pressure of the secondary fluid introduced into said sample tube is relatively higher than the pressure of the secondary fluid introduced into said housing.

5. In a probe for sampling a primary gas flowing in a pipe, said probe comprising a sample tube having a first end extending through the wall and into the interior of the pipe and a second end located outside of the pipe, a filter attached to the first end of said sample tube, and a source of vacuum for withdrawing a portion of the primary gas in the pipe through said filter and said sample tube, the improvement wherein said probe further comprises:
   a. a housing extending into the pipe and surrounding that portion of the sample tube located outside the pipe, said housing being in substantially gas-tight association with the walls of the pipe and having at least one orifice connecting the interior of said housing to the interior of the pipe at a position remote from said filter;
   b. a source of relatively high pressure, temperature controlled secondary gas; and
   c. a variable setting, four-port, plug valve disposed within said housing, said valve, at one setting, connecting said source of vacuum to the second end of said sample tube and said source of secondary gas to the interior of said housing, and, at another setting, connecting said source of secondary gas to the second end of said sample tube and said source of vacuum to the interior of said housing.

6. The probe of claim 5 further comprising a calibration valve located in said sample tube and disposed in said housing, and a calibration inlet connected to said calibration valve.

7. In a method of sampling a primary fluid located in a confined region defined by at least one wall comprising the steps of providing a sample tube with a first end having a filter attached thereto and extending through the wall into the confined region and a second end located outside the confined region, and withdrawing a portion of the primary fluid from the confined region through the filter and the sample tube, the improvement comprising the steps of:
   a. providing a housing extending through the wall into the confined region and surrounding that portion of the sample tube located outside of the confined region, the housing being in substantially fluid-tight association with the wall and having at least one orifice connecting the interior of the housing with the confined region at a position remote from the filter;

b. introducing a relatively high pressure, controlled temperature, secondary fluid into the housing to control the temperature of the sample tube and the fluid being withdrawn through it; and c. alternately introducing the secondary fluid into the second end of the sample tube to backflush the filter.

8. In a method of sampling a primary fluid located in a confined region defined by at least one wall comprising the steps of providing a sample tube with a first end having a filter attached thereto and extending through the wall into the confined region and a second end located outside the confined region, and applying a vacuum to the second end of the sample tube to withdraw a portion of the primary fluid from the confined region through the filter and the sample tube, the improvement comprising the steps of:

a. providing a housing extending through the wall into the confined region and surrounding that portion of the sample tube located outside of the confined region, the housing being in substantially fluid-tight association with the wall and having at least one orifice connecting the interior of the housing with the confined region at a position remote from the filter;

b. introducing a relatively high pressure, controlled temperature, secondary fluid into the housing to control the temperature of the sample tube and the fluid being withdrawn through it; and c. alternately introducing the secondary fluid into the second end of the sample tube to backflush the filter and at the same time venting the vacuum.

9. In a method of sampling a primary gas flowing through a pipe, comprising the steps of providing a sample tube with a first end having a filter attached thereto and extending through the wall and into the interior of the pipe and a second end located outside the pipe, and applying a vacuum to the second end of the sample tube to withdraw a portion of the primary gas from the pipe through the filter and the sample tube, the improvement comprising the steps of:

a. providing a housing extending through the walls of the pipe and surrounding that portion of the sample tube located outside the pipe, the housing being in substantially leak-tight association with the walls of the pipe and having at least one orifice connecting the interior of the housing to the interior of the pipe at a position remote from the filter;

b. introducing a relatively high pressure, controlled temperature secondary gas into the housing to control the temperature of the sample tube and the fluid being withdrawn through it; and c. periodically introducing the secondary fluid into the second end of the sample tube to backflush the filter and, at the same time, venting the vacuum to the interior of the housing and into the pipe.

* * * * *